United States Patent [19]

Anderson et al.

[11] 3,954,759

[45] May 4, 1976

[54] PROCESS FOR PREPARATION OF 6-SUBSTITUTED 5-FLUOROURACIL DERIVATIVES

[75] Inventors: Roy Anderson, Gainsville; Paul D. Schuman, Hawthorne, both of Fla.

[73] Assignee: PCR, Inc., Gainesville, Fla.

[22] Filed: July 13, 1972

[21] Appl. No.: 271,490

[52] U.S. Cl. .......................... 260/260; 260/256.4 C; 424/251
[51] Int. Cl.² ........................................ C07D 239/22
[58] Field of Search ...................... 260/260, 256.4 C

[56] References Cited
UNITED STATES PATENTS 3,221,010  11/1965  Duschinsky et al................. 260/260
3,277,092  10/1966  Duschinsky et al................. 260/260
3,682,917  8/1972  Knuniants et al................... 260/260

*Primary Examiner*—Paul M. Coughlan, Jr.
*Attorney, Agent, or Firm*—Murray and Whisenhunt

[57] ABSTRACT

The reaction of certain fluorinated pyrimidine derivatives with hydrogen donor compounds to produce 6-substituted 5-fluoropyrimidines is disclosed. The products so produced are useful in germicidal and antineoplastic applications, and can be converted into 5-fluorouracil, which has known utility in cancer chemotherapy.

12 Claims, No Drawings

3,954,759

PROCESS FOR PREPARATION OF 6-SUBSTITUTED 5-FLUOROURACIL DERIVATIVES

BACKGROUND OF THE INVENTION

The present invention relates to a novel process for preparing 6-substituted 5-fluoro-uracil and -cytosine derivatives.

Uracil has been reacted with various compounds to achieve substitution in the 5 position, see "Chlorination of 2,4-Diketotetrahydropyrimidines by Action of Mixture of Superoxol and Hydrochloric Acid", Journal of the American Chemical Society, Vol. 65, part 1, pp. 1218–1219 (1943); "Action of Alkali and Ammonia on 2,4-Dialkoxypyrimidines", Journal of the American Chemical Society, Vol. 56 part 1, pp. 134–139 (1934); "The Reaction of Bromine with Uracils", Journal of Organic Chemistry, Vol. 24, p. 11, Jan. 1959; Wang, "Reaction of Bromine with Uracils", Nature 180, pp. 91–92 (July 13, 1957) and Brown infra.

The reaction of bromine or chlorine with uracil is as follows:

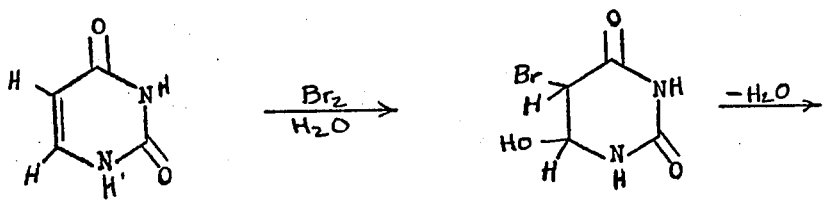

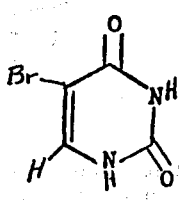

Numerous references may be cited which demonstrate the extreme reactivity of fluorine in contrast to the other halogens. For example, see M. Hudlicky, "Chemistry of Organic Fluorine Compounds", The MacMillan Co., New York (1962) and J. H. Simons, "Fluorine Chemistry", Vol. 1, Academic Press, Inc., New York, New York (1950). This extreme reactivity and the presumed required intermediacy of a hypohalous acid addition to the double bond would preclude the predictability of the reaction product of the aqueous fluorination of uracil.

The reaction of elemental fluorine with organic compounds has been studied extensively since the discovery of the gas by Henri Moissan in 1886. Moissan found that unlike chlorine, bromine and iodine, the unmoderated reaction of fluorine with organic compounds results in ignition and ultimate decomposition of the organic compound to smaller molecules. This greatly increased reactivity of fluorine compared to the other halogens is readily explained by comparing the heats of reaction of the halogens as in the following reactions. See M. Hudlicky, "Chemistry of Organic Fluorine Compounds", p. 72, The MacMillan Co., New York (1962).

| | X = F | H° (K cal/mole) Cl | Br | I |
|---|---|---|---|---|
| $C=C + X_2 \rightarrow CX-CX$ | −107.2 | −33.1 | −18.8 | + 1.2 |
| $C-H + X_2 \rightarrow C-X+HX$ | −102.5 | −22.9 | − 6.2 | +13.7 |

Since the carbon-carbon bond energy is only about 60 K cal/mole, it is quite evident that unless the heat of reaction is removed rapidly the heat evolved in fluorination is more than sufficient to destroy the carbon skelton.

A number of methods have been used in which the heat of reaction is dissipated rapidly enough to give fair yields of fluorinated product. The more common methods are: (1) bubbling a mixture of fluorine and an inert gas through a cold liquid; (2) conducting away the heat of reaction by conducting the reaction in the presence of metal packing; and (3) addition of very large amounts of an inert diluent gas. See M. Stacey, J. C. Tatlow, and A. G. Sharpe, "Advances in Fluorine Chem.", Vol. 2, pp. 196–208, Butterworth, Inc., Washington, D.C. (1961); M. Hudlicky, "Chemistry of Organic Fluorine Compounds", The MacMillan Co., New York (1962); and J. H. Simons, "Fluorine Chemistry", Vol. 1, Academic Press, Inc., New York, N.Y. (1950).

An aqueous medium has seldom been used to assist in fluorination of organic compounds. Reference may be made to the work of Banks, Haszeldine and Lalu, Chem. and Ind. (London), 1803 (1964), CA 62, 428 g. (1965), in which esters of carbamic acid were fluorinated.

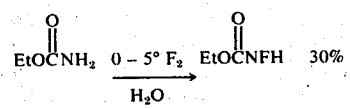

Since uracil exists predominately in the oxo or keto form, see D. J. Brown, "The Pyrimidines", p. 9, Interscience Publishers, Inc., New York (1962), the results of Bank's work would lead one to believe that fluorination of uracil would result in N fluorination rather than C fluorination, i.e., would yield products containing N-F groups. Early work of Heidelberger and Duschinsky reported in U.S. Pat. Nos. 2,802,005 and 3,201,387 indicate that various 6-substituted uracil derivatives are known. Of particular interest is the preparation of 5-fluorocytosine disclosed in the former patent and prepared by refluxing 2-ethylmercapto-4-amino-5-fluoropyrimidine in concentrated aqueous hydrobromic acid. The resulting 5-fluorocytosine and the salts thereof are useful as antimetabolites and to inhibit the growth of various microorganisms. 5-fluorocytosine is a basic compound readily reacting to form addition salts with mineral acids to form pharmaceutically acceptable non-toxic salts. Suitable mineral acids are hydrochloric acid, hydrobromic acid, sulfuric acid, nitric acid, phosphoric acid. Organic acids such as ethanesulfonic acid, toluenesulfonic acid, tartaric acid, citric acid and the like are also used.

It is also known to prepare 5-fluorouracil by reacting uracil mixed with a diluent amount of acetic acid or anhydrous hydrofluoric acid and treating the mixture with fluorine mixed with nitrogen as an inert gas at a temperature of 20° to 25°C; see Belgian Pat. No. 748,468 to Knuniants et al. However, the yield of 5-fluorouracil produced by this process is generally low and the presence of the diluents in the reaction mixture tends to give rise to undesirable secondary reaction products.

As previously stated, the process of the present invention is useful for the preparation of 6-substituted 5-fluoropyrimidine derivatives. The use of 5-fluorouracil in the treatment of cancer, particularly dermatological cancers, is known and well documented. See Heidelberger et al, "Studies on Fluorinated Pyrimidines II — Effects on Transplanted Tumors", Cancer Research, Vol. 18, p. 305 (1958), and Heidelberger et al, "Fluorinated Pyrimidines, A New Class of Tumor-Inhibitory Compounds", Nature, Vol. 179, p. 663, Mar. 30, 1957. Bardos et al Nature 183, 612 (1959), and Brown, D. J. "The Pyrimidines", p. 175, Interscience, New York (1962). Similarly various cytosine derivatives have been found to be effective antineoplastic and antiviral agents.

The commercially employed method for the synthesis of 5-fluorouracil disclosed in aforesaid U.S. Pat. No. 2,802,005 utilizes extremely toxic monofluoro intermediates. See Stacy et al, "Advances in Fluorine Chemistry", Vol. 2, pp. 196–208, Butterworth, Washington, D.C. (1961). Large scale production has not been undertaken primarily because of the difficulty in handling these intermediates.

It is also known to prepare various uracil derivatives by reacting 5-fluorouracil with chlorine or bromine in the presence of water, as disclosed in Duschinsky et al U.S. Pat. No. 3,277,092. The reaction may be described by the following scheme:

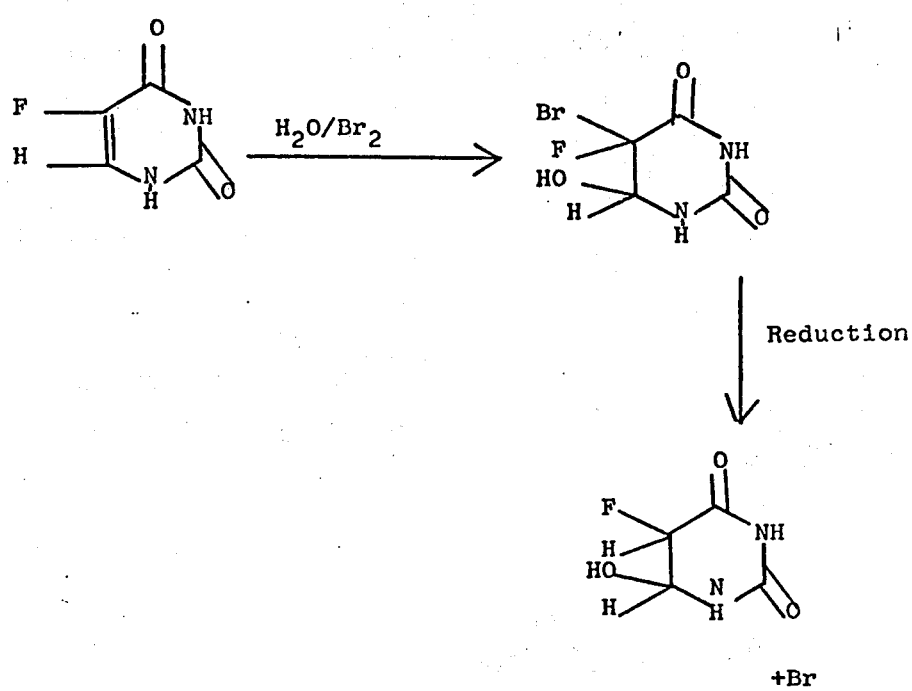

This procedure requires a separate reduction step to remove the bromine, or chlorine, as the case may be, to produce the uracil derivative, in this case 5-fluoro-6-hydroxy-5,6-dihydrouracil.

DETAILED DESCRIPTION OF THE INVENTION 6-substituted 5-fluoropyrimidines can be produced by reacting certain nucleophilic reagents, such as compounds containing active hydrogen atoms, with certain pyrimidine derivatives having a 6-fluoro or a 6-acyloxy substituent thereon.

The 6-substituted 5-fluoropyrimidines which are produced by the process of the present invention can be conveniently represented by the following formula:

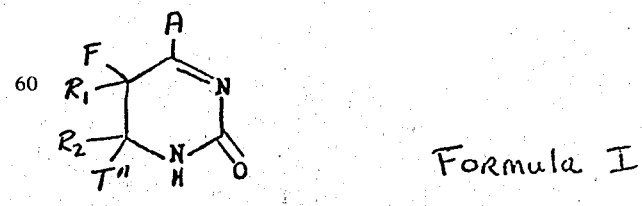

wherein A is —OH or —NH$_2$, R$_1$ is hydrogen, fluorine, chlorine, bromine or lower alkyl, R$_2$ is hydrogen or lower alkyl, and T'' is defined hereinafter. The formula illustrates the substituted pyrimidine product in one tautomeric form and it is clear that the product can exist in another tautomeric form —e.g., as a uracil derivative.

The 6-substituted pyrimidine derivatives which are used as starting materials are of the following formula:

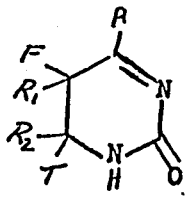

Formula II wherein A is —OH or —NH$_2$; R$_1$ is hydrogen, fluorine, chlorine, bromine or lower alkyl; R$_2$ is hydrogen or lower alkyl; and T is F or lower acyloxy, including lower haloacyloxy. The above formula illustrates the pyrimidine compounds in one tautomeric form, and it is clear that the starting materials can exist as the other tautomer. Thus, the pyrimidine derivatives used in the present invention are generally uracil or cytosine derivatives, depending upon whether A is hydroxyl or amino, respectively. Preferably, T is fluorine or lower fluoroacyloxy, and more preferably T is trifluoroacetoxy. Preferably, A is —OH, and more preferably R$_1$ and R$_2$ are both hydrogen. Mixtures of starting materials may be used.

The fluorinated pyrimidine derivative starting materials of the above formula are reacted with a nucleophilic reagent which is a compound having an active hydrogen, such as water, alcohols, mercaptans, acids, or primary or secondary amines. The active hydrogen-containing nucleophilic reagent is preferably of the formula T"H, wherein T" is represented by the following structural formulae, which formulae also represent the substituent in the six-position of the substituted pyrimidines produced according to the present invention:
—OH
—OC(R')$_3$
—SR
—OOCR'
—NRR'
wherein R is selected from the group consisting of alkyl of 1 – 6 carbon atoms and lower cycloalkyl of 3 – 6 carbon atoms, wherein one or more hydrogen atoms of the alkyl or cycloalkyl radicals may be replaced by fluorine, chlorine or bromine atoms, and R' is R or hydrogen. Preferably, the active hydrogen-containing nucleophilic reagent is an acid or alcohol, with the most preferred compounds being alcohols such as trifluoroethanol, trifluorobutanol, and the like.

Typical examples of active hydrogen-containing nucleophilic reagents which can be represented by the formula T"H include water, methanol, trifluoroethanol, butyl mercaptan, acetic acid, propionic acid, butyl amine, methylethyl amine and the like.

The pyrimidine derivative starting material is reacted with the nucleophilic reagent at a temperature of −10° to 72°C., preferably 20° to 60°C, most preferably at about room temperature. The reaction proceeds readily at atmospheric pressure, although higher or lower pressures may be used if desired. Generally at least stoichiometric amounts of the nucleophilic reagent will be used, and preferably a stoichiometric excess of the nucleophilic reagent is utilized. There is no upper limit to the amount of nucleophilic reagent which can be used, but for economic reasons generally the molar ratio of nucleophilic reagent to pyrimidine derivative will not exceed 100:1. More preferably, the molar ratio of nucleophilic reagent to pyrimidine derivative will be from about 1.01:1 to about 10:1.

The 6-substituted pyrimidine derivatives produced by the process of the present invention are normally readily separated from the reaction mixture. In some instances, such as in the production of 5-fluoro-6-methoxy-5,6-dihydrouracil, a precipitate will form which can be isolated by filtration and washing. In other instances, a solution of the 6-substituted pyrimidine derivative will be formed in excess nucleophilic reagent, and the excess nucleophilic reagent can be removed by, e.g., distillation.

The 6-substituted pyrimidine derivatives which are used as starting materials in the process of the present invention may be readily produced by the process described in the copending application of Paul D. Schuman, Geraldine Westmoreland and Roy Anderson, Ser. No. 271,489, filed July 13, 1972, entitled "5-Fluorouracil Derivatives and Process for Producing 5-Fluorouracil and Derivatives Thereof in Acid and/or Alcohol Solvents", the disclosure of which is hereby incorporated by reference to the extent necessary to understand the production of the preferred starting materials of the process of the present invention. Briefly, the disclosure of the aforesaid copending patent application includes the preparation of 6-substituted pyrimidine derivatives by fluorinating, in a solvent having the formula

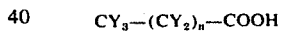
CY$_3$—(CY$_2$)$_n$—COOH wherein each Y is independently selected from the group consisting of hydrogen, chlorine or fluorine, and n is a number from 0 to 6, a pyrimidine derivative having the formula

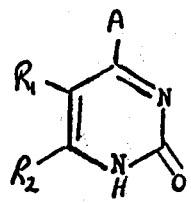

Formula III with at least a stoichiometric amount of gaseous fluorine, at a temperature from about the solvent freezing point to about 25°C., preferably from 0° to 25°C. and more preferably from 0° – 2°C., wherein R$_1$ is hydrogen, fluorine, chlorine, bromine or lower alkyl, R$_2$ is hydrogen or lower alkyl, and A is OH or NH$_2$. The reaction should be conducted in an inert system, such as in a Teflon-lined system, in order for the intermediate products to be readily isolated. Intermediate compounds having the structure of Formula II will be produced, generally in a mixture of such compounds, wherein some of the compounds in the mixture have the structure of Formula II wherein T is F, and other of the compounds in the mixture have the structure of Formula I wherein T is acyloxy. For instance, when fluorinating uracil with gseous fluorine in trifluoroacetic acid at about 0°C., the resulting reaction mixture contains 5,6-difluoro-5,6-dihydrouracil and 5-fluoro-6-trifluoroacetoxy-5,6-dihydrouracil, in an approximately 2:1 ratio of the difluoride intermediate to the acetoxy intermediate, although this molar ratio will depend upon the particular reaction conditions used. The identification of these intermediate compounds has been confirmed by NMR analyses of solutions of such compounds. When the reaction is conducted in an inert system, the solid intermediate compounds can be isolated, but the NMR analyses for such isolated compounds have generally been inconclusive. However, infrared analysis indicates that the solid isolated intermediate product is not 5-fluorouracil and heating the intermediate product produces 5-fluorouracil, with evolution of trifluoroacetic acid and hydrofluoric acid, all of which is consistent with the NMR results obtained for the solutions mentioned above.

It is a well-known fact that the bromination or chlorination of uracil in an organic acid solvent involves the intermediate formation of a hypohalite, with the hypohalite then reacting with uracil to produce the corresponding 5-halo-6-acyloxy derivative. Although unexpected, the similarity of the fluorinated products of Formula II clearly shows the intermediacy of a hypofluorite as one of the reaction paths in the fluorination reaction described hereinabove. In the fluorination reaction, the fluorine reacts with the acid solvent to produce an acid hypofluorite of the formula

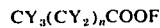

The existance of an acid hypofluorite, e.g. trifluoroacetyl hypofluorite, has been confirmed by Cady, J. Amer. Chem. Soc. 75, 2501 (1953).

Illustrative, but non-limiting, examples of suitable solvents include propionic, n-butyric, isobutyric, n-valeric, isovaleric, methylethylacetic, trimethylacetic, caproic, heptoic and caprylic acids. Preferably at least some of the hydrogen atoms are replaced by fluorine, chlorine or bromine atoms. The preferred acid reaction solvents are halogenated acids, especially fluorinated acids, most preferably polyfluorinated acids, including trichloroacetic acid, trifluoropropionic acid and trifluoroacetic acid. Thus poly-fluorinated acids are preferred over the hydrocarbon acids in general, as the hydrocarbon acids have been found to be somewhat less attractive owing to highly toxic monofluorinated acid by-products that may be present in the reaction mixture and also owing to inherently slow reaction rates.

The above general solvent formula is presented as an atomic rather than configurational display of suitable solvents, as it will be appreciated that the acids used may be straight chained or branched. Although it is contemplated that higher chain length halogenated acids may be used, these are at present difficult to obtain commercially and thus the above description is directed to the lower chain lengths. As the halogen substituents there may be mentioned chlorine, bromine and fluorine.

As used herein, lower alkyl generally designates an alkyl group having from 1 to 6 carbon atoms such as methyl, ethyl, propyl, butyl, hexyl, etc., and the position isomers thereof, including halogen substituted lower alkyl groups, such as chloroethyl, bromopropyl, etc, especially trifluoromethyl.

The overall reaction scheme is believed to occur substantially as follows, wherein uracil is the pyrimidine ring illustrated and the fluorination is in a trifluoroacetic acid reaction medium:

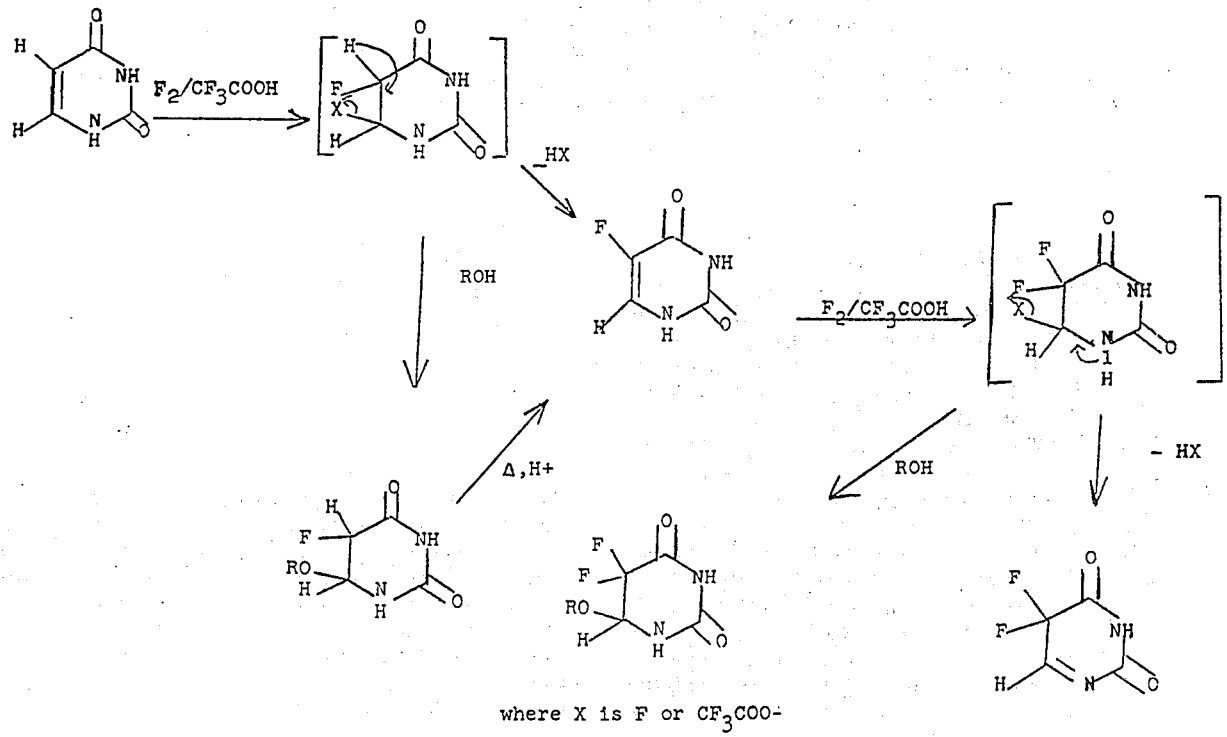

where X is F or $CF_3COO^-$

From the above, it is believed that the formation of 6-substituted compounds occurs through two intermediates, both of which are formed as follows, again illustrated with uracil as the starting pyrimidine compound and trifluoroacetic acid as the solvent:

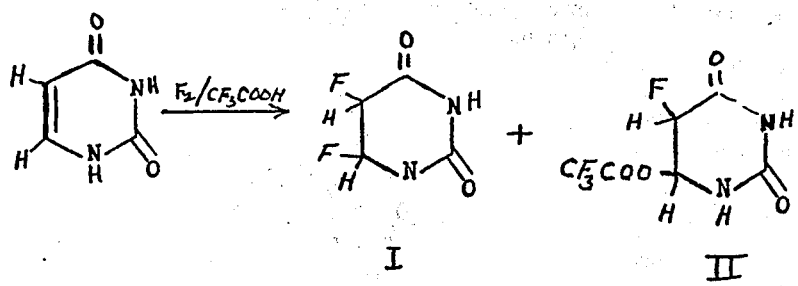

Product I or II or their mixture is then reacted with a hydrogen donor to give the desired 6-substituted derivative. For instance, these intermediate products are reacted with trifluoroethanol to produce the corresponding 6-trifluoroethoxy derivative. Intermediate products I and II are readily isolated from solution and separated as solid products, thus providing a convenient source of starting materials.

Thus, the preferred embodiment of the present invention involves first forming an intermediate product by the process discussed in application Ser. No. 271,489, and then reacting such intermediate product with at least one compound of the formula T"H. The overall process involves the reaction of a compound of Formula III with gaseous fluorine in the presence of the above-identified solvents to produce intermediate compounds having the structure of Formula II. Then the intermediate compounds of Formula II are reacted with the active hydrogen-containing nucleophilic reagent having the formula T"H. In the process of the present invention it is unnecessary to isolate the intermediate compounds, although in some instances it may be found preferable to isolate the dry intermediate product.

As set forth in the aforesaid application, the prior art was unaware that the intermediate products described hereinabove could be isolated per se. This approach is particularly attractive where a number of pyrimidine derivatives are to be produced, as the intermediate product can be isolated and stored, generally under low temperature conditions, until such time as it is desired to convert the intermediate product into one or more of a wide variety of 5-fluorinated 6-substituted pyrimidine derivatives.

Aryl-substituted pyrimidine derivatives have not been discussed in the foregoing description of the present invention, due to the general unavailability of such aryl-substituted pyrimidine derivatives. However, the results obtained above suggest that the process of the present invention can also be used to produce 6-substituted pyrimidine derivatives having one or more aryl substituents on the 1,3,5 and/or 6 positions, using corresponding starting compounds. Examples of such aryl groups are phenyl and ortho-, meta-, and para-substituted phenyl groups carrying substituents such as $-NO_2$, $-SO_3H$, $-SO_3Na$, $-NH_2$, $-OH$, halogen and the like. Similarly, starting materials having the 1 and/or 3 nitrogen atoms substituted with lower alkyl groups, or having lower alkyl substituents on the nitrogen atom attached to the 4-position carbon atom of a cytosine derivative, have not been described due to the general commercial unavailability of such compounds, but these compounds should also undergo the reaction described hereinabove according to the process of the present invention.

The compounds produced by the process of the present invention are useful in germicidal and antineoplastic applications. For instance, such compounds are active against gram negative and gram positive bacteria and against yeasts and fungi. This is in agreement with the use of other uracil derivatives disclosed in U.S. Pat. No. 3,277,092, the disclosure of which is hereby incorporated by reference. Due to their structural similarity to 5-fluorouracil, the compounds produced by the process of the present invention appear to be useful in cancer chemotherapy, especially the 6-substituted uracil derivatives and, in particular, 5,5-difluoro-6-hydroxy-5,6-dihydrouracil. The disclosures of Japanese Pat. Nos. 18946/66 and 19845/66 are hereby incorporated by reference for the teachings therein of utilities for certain of the compounds produced by the process of the present invention.

Another embodiment of the present invention is directed to the production of high purity 5-fluorouracil and derivatives thereof. The 5-fluorouracil or 5-fluorouracil derivataive may be produced directly from the starting materials of Formula II, by sublimation or by refluxing in the presence of a strong acid. Generally, the sublimation will be at a temperature above about 100°C up to the decomposition temperature of the compound or compounds involved. Preferably sublimation is at a temperature of about 150° — about 250°C, more preferably about 190°C. Generally, the sublimation will be conducted under reduced pressures, peferably under pressures less than 50 mm of Hg, more preferably less than 10 mm of Hg, and most preferably about 1 mm Hg. It will be appreciated, however, that ambient pressures may be used in the sublimation step.

If the compounds of Formula II are to be converted to 5-fluorouracil or derivative thereof by elimination with the use of a strong acid, such as concentrated hydrochloric acid or strong aqueous sulphuric acid solutions (generally above 5% by weight sulphuric acid solution), it is preferred to operate under refluxing conditions. In general, temperatures substantially below refluxing temperatures will require too much time for the elimination step, whereas temperatures substantially above refluxing conditions involve no significant advantage. However, it will be appreciated that it is possible to operate the elimination step at temperatures above or below the refluxing temperature, e.g., 60° – 130°C. Likewise, although it is preferred to conduct the elimination step in the strong acid under ambient pressure, higher or lower pressures may be used if desired. Generally, at least a stoichiometric amount of the strong acid will be used, and peferably a stoichiometric excess of the strong acid is used. There is no upper limit on the amount of acid which can be used, but it will be appreciated that no significant advantages are derived from using too great an excess of the acid. For this reason, the amount of acid used will generally be less than 10 times the stoichiometric amount.

A more preferred method of producing 5-fluorouracil or derivatives thereof of high purity involves the elimination of T'' from compounds of Formula I to produce 5-fluorouracil and derivatives thereof. An especially preferred embodiment involves the use of compounds of Formula I, wherein T'' is —OCH$_2$R' (the starting compounds contain a 6-alkoxy substituent). Such 6-alkoxy-5-fluorouracil compounds may be readily purified, permitting the subsequent production of 5-fluorouracil and derivatives thereof of high purity. For instance, the 6-alkoxy-5-fluorouracil compounds may be readily recrystallized with a suitable solvent, e.g. an alcohol, such as ethanol, to a high level of purity.

The compounds of Formula I, and especially the 6-alkoxy-substituted compounds, may be readily converted into 5-fluorouracil or derivatives thereof by sublimation or elimination with a strong acid using the conditions described above for the compounds of Formula II. When using the strong acid elimination, the elimination temperature will normally be in the range of 60°– 130°C, although even higher temperatures may be used. Preferably, the elimination temperature will be about 90°– 95°C.

The elimination reactions described hereinabove involve the elimination of compounds of the formula TH or T''H. At least one of R$_1$ and the 1-position nitrogen atom substituent must be hydrogen. If R$_1$ is hydrogen, TH or T''H will eliminate, with formation of a 5,6 double bond. If, on the other hand, R$_1$ is not hydrogen, then the elimination of TH or T''H will produce a 1,6 double bond.

Thus, the process for producing 5-fluorouracil and derivatives thereof, and 5-fluorocytosine and derivatives thereof involves reacting, in a solvent having the formula $$CY_3—(CY_2)_n—COOH$$

wherein each Y is independently selected from the group consisting of hydrogen, chlorine and fluorine and $n$ is a number from 0 – 6, at a temperature from about the solvent freezing point to about the solvent boiling point, a compound of the formula:

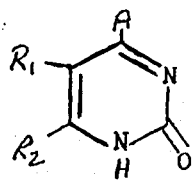

wherein A is —OH or —NH$_2$, R$_1$ is hydrogen, fluorine, chlorine, bromine or lower alkyl and R$_2$ is hydrogen or lower alkyl, with at least about a stoichiometric amount of gaseous fluorine, to produce a reaction product, thereafter isolating the reaction product from excess solvent and the like to produce said reaction product in the form of a dry solid. The dry solid reaction product, which generally is of Formula II above, can be directly converted into 5-fluorouracil or derivatives thereof (or 5-fluorocytosine and derivatives thereof), or the isolated, dry reaction product can be converted into another 5-fluoro-6-substituted pyrimidine compound, which then is converted into the desired final product by an elimination reaction. The final product is of the formula

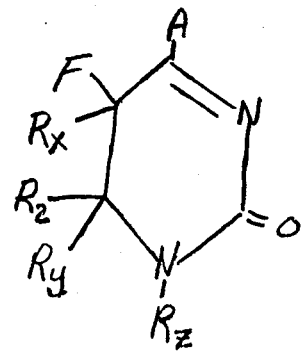

wherein A and R$_2$ are defined hereinabove, R$_X$ is fluorine, chlorine, bromine, lower alkyl or, taken with R$_Y$ a 5,6-double bond, R$_Y$ is a 5,6-double bond taken with R$_X$ or a 1,6-double bond taken with R$_2$ and R$_Z$ is hydrogen or a 1,6-double bond taken with R$_Y$.

The isolated dry reaction product is preferably of the Formula II above, and the desired final product can be produced by eliminating TH from the isolated dry reaction product. The elimination of TH can be accomplished by subliming the dry reaction product at a temperature of about 150° to about 250°C and a pressure of less than 50 mm of Hg, or by refluxing the compound of Formula II in at least a stoichiometric amount of a strong acid.

In the alternative embodiment, the compound of Formula II is reacted at a temperature of −10° to 72°C. with a compound of the formula T''H wherein T'' is —OH, —OCH$_2$R', —OOCR', —NRR, wherein R is selected from the group consisting of lower alkyl and lower cycloalkyl, wherein one or more hydrogen atoms of the alkyl or cycloalkyl may be replaced by fluorine, chlorine or bromine atoms, and R' is R or hydrogen to produce a 5-fluoro-6-substituted pyrimidine compound of the formula

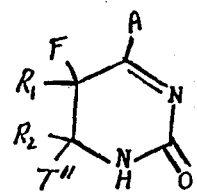

wherein A, T'', R$_1$ and R$_2$ are defined above, and then eliminating T''H from said 5-fluoro-6-substituted pyrimidine compound by subliming said compound at a temperature of about 150°— about 250°C and a pressure of less than 50 mm of Hg, or refluxing said 5-fluoro-6-substituted pyrimidine compound in at least a stoichiometric amount of a strong acid.

5-fluorouracil is a known compound having recognized utility. For instance, 5-fluorouracil is widely used in cancer chemotherapy.

EXAMPLES OF THE INVENTION

The invention will be understood more readily by reference to the following examples; however, these examples are intended to illustrate the invention and are not to be construed to limit the scope of the invention. All parts and percents are expressed by weight unless otherwise indicted.

EXAMPLE A (Preparation of starting materials 5-Fluoro-6-trifluoroacetoxy-5,6-dihydrouracil and 5,6-Difluoro-5,6-dihydrouracil)

1. 20 g of uracil (0.178 moles) and 130 ml of trifluoroacetic acid were added to a 1″ diameter Teflon-lined reactor, equipped with a cooling jacket and a bottom gas inlet tube. The resulting slurry was cooled to 0°C and fluorine, diluted with an about equal volume of nitrogen, was passed through the slurry at a gas flow rate of approximately 75 cc/min. The reactor contents were maintained at a temperature of 0°C and fluorination was continued for 66 minutes, resulting in a consumption of 9.17 g of fluorine (0.241 moles). NMR analysis of the reaction mixture indicated the presence of 5,6-difluoro-5,6-dihydrouracil and 5-fluoro-6-trifluoroacetoxy-5,6-dihydrouracil, in an approximate molar ratio of 2:1 respectively.

2. The reaction mixture produced in step 1 above was divided in half and the trifluoroacetic acid was evaporated from one of the reaction mixture portions, to produce a white solid product mixture. A smaller portion of this white solid product mixture was heated to about 100° to produce, as the major nonvolatile product, 5-fluorouracil, with evolution of trifluoroacetic acid and hydrofluoric acid.

EXAMPLE 1

(5-Fluoro-6-methoxy-5,6-dihydrouracil)

A. 20 ml of methanol were added to 10 ml of the reaction mixture obtained in Example A1 above, at ambient conditions, whereupon a slight exotherm occurred, with precipitation of solid material. The solid material was removed by filtration, washed with methanol, and dried under vacuum at room temperature, producing a white crystalline solid product. This product showed two DSC transitions at 193°C and 282°C. Analysis calc. for $C_5H_7N_2O_3F$: C, 37.0; H, 4.32; N, 17.3. Found: C, 36.1; H, 4.2; N, 17.7.

B. 0.5 g of solid product mixture obtained in Example A2 was added to 1.5 ml of methanol and warmed until a clear solution was obtained. Then the mixture was cooled to 0°C, and filtered, with a white solid product obtained. The infrared spectrum of this white solid product was identical to that of the 5-fluoro-6-methoxy-5,6-dihydrouracil obtained in Example 1A above.

EXAMPLE 2

(5-Fluoro-6-(2,2,2-trifluoroethoxy)-5,6-dihydrouracil)

A. 8 ml of the reaction solution obtained in Example A1 above were added to an excess (10 ml) of 2,2,2-trifluoroethanol in a 25 ml Erlenmeyer flask at room temperature, with a slight exotherm noted. The volatile material was evaporated to produce white crystalline 5-fluoro-6-(2,2,2-trifluoroethoxy)-5,6-dihydrouracil that showed a DSC transition at 270°C. Anal. calc. for $C_6H_6N_2O_3F_4$: C, 31.3; H, 2.61; n, 12.2. Found: C, 29.84; H, 2.66; N, 13.3.

B. Example 1B was repeated, substituting 2,2,2-trifluoroethanol for the methanol. The resulting product exhibited infrared absorption maxima essentially identical to that obtained in Example 2A above.

EXAMPLE 3

(5-Fluoro-6-acetoxy-5,6-dihydrouracil)

2 ml of acetic acid were added to 1g of the solid product mixture obtained in Example A2 above in a 25 ml Erlenmeyer flask at room temperature. The mixture was warmed until the solid product dissolved in the acetic acid. The acetic acid was then evaporated, yielding a crystalline solid product which was identified as 5-fluoro-6-acetoxy-5,6-dihydrouracil. An infrared spectrum of this product showed a doublet at 5.7 and 5.8 microns.

EXAMPLE 4

(5-Fluoro-6-isopropoxy-5,6-dihydrouracil)

A. 5 ml of the reaction solution obtained in Example A1 above was placed in a 25 ml Erlenmeyer flask, and 20 ml of isopropyl alcohol were added to the flask, at room temperature. A slight exotherm occurred, with precipitation of solid material. The solid material was removed by filtration, washed with isopropanol and dried under vacuum at room temperature, yielding 5-fluoro-6-isopropoxy-5,6-dihydrouracil, a white crystalline solid which showed a DSC transition at 276°C. Analysis calc. for $C_7H_{11}N_2O_3F$: C, 44.2; H, 5.8; N, 14.8. Found: C, 40.7; H, 5.2; N, 13.8.

B. Example 1B was repeated, except isopropanol was used in place of the methanol, producing a white crystalline product which exhibited an identical infrared spectrum to the product obtained in Example 4A above.

EXAMPLE 5

(5-Fluoro-6-hydroxy-5,6-dihydrouracil)

1.5 cc of water was added to 1.0 g of solid product obtained in Example A2 above. The mixture was heated slightly until the solids were completely in solution, and then the solution was held overnight at 0°C. A white precipitate formed, which was removed by filtration. The white precipitate was identified, by comparison with a known sample, as 5-fluoro-6-hydroxy-5,6-dihydrouracil.

EXAMPLE 6

(5-Fluoro-6-ethylthio-5,6-dihydrouracil)

A. 5 ml of the reaction solution obtained in Example A1 above were added to 5 ml of ethyl mercaptan in a 25 ml Erlenmeyer flask at room temperature. The volatile material was then removed by placing the flask contents under a vacuum of 1 mm of mercury at room temperature, leaving a white crystalline solid which was identified as 5-fluoro-6-ethylthio-5,6-dihydrouracil. Anal. calc. for $C_6H_9N_2O_2SF$: C, 37.5; H, 4.7; N, 14.6. Found: C, 34.4; H, 3.94; N, 14.52.

B. Example 1B was repeated, using ethyl mercaptan in place of the methanol. A product was obtained which was similar to the product of Example 6A above.

EXAMPLE 7

(5-Fluoro-6-(1,1,1,3,3,3-hexafluoroisopropoxy)-5,6-dihydrouracil)

5 ml of the reaction solution obtained in Example A1 above were added to 20 ml of 1,1,1,3,3,3-hexafluoroisopropanol in a 25 ml Erlenmeyer flask at room temperature. No exotherm was noted. The volatile materials were then evaporated from the flask, leaving a white crystalline product which was identified as 5-fluoro-6-(1,1,1,3,3,3-hexafluoroisopropoxy)-5,6-dihydrouracil.

EXAMPLE 8

(5-Fluoro-6-diethylamino-5,6-dihydrouracil)

1g of solid product obtained in Example A2 above was added to 2 ml of dimethylamine at room temperature, with an exothermic reaction noted. After the exotherm subsided, the excess dimethylamine was evaporated, yielding 5-fluoro-6-diethylamino-5,6-dihydrouracil.

EXAMPLE 9

(5-Fluoro-6-cyano-5,6-dihydrouracil)

2g of sodium cyanide was added to 10 ml of reaction solution obtained in Example A1 above. Upon removal of excess sodium cyanide, a product was obtained which showed an infrared absorption maxima different from the starting material, and the identification assigned this product was 5-fluoro-6-cyano-5,6-dihydrouracil.

EXAMPLE 10

(Trifluoroacetic acid salt of 5-fluoro-6-hydroxy-5,6-dihydrocytosine)

11.2 g of cytosine (0.1 moles) and 56 g of trifluoroacetic acid were added to a 20 mm diameter Pyrex tube equipped with a gas bubbler in a water bath maintained at a temperature of 37°– 42°C. Fluorine gas diluted with an approximate equal volume of nitrogen was passed through the tube contents at a rate of 28 cc per minute for 178 minutes, corresponding to approximately 0.2 moles of fluorine. Initially the reaction temperature increased to 50°C, but thereafter the tube contents were maintained at about the water bath temperature. During the course of the reaction, additional trifluoroacetic acid was added to replace evaporated solvent. Total solids in the tube, calculated from results of evaporating an aliquot sample, amount to 29.4 g.

A. 10 ml of water was added to 14 g of the reaction solution. The slightly cloudy resulting solution was filtered and then evaporated to dryness yielding 5.7 g of a tacky solid. 20 g of water was added to 5 g of this tacky solid, and the resulting solution was evaporated to dryness, and then the resulting solids were recrystallized from water to yield light tan needle crystals of the trifluoro acetic acid salt of 5-fluoro-6-hydroxy-5,6-dihydrocytosine, which sublimed at 328°C.

B. The remainder of the reaction solution was evaporated to dryness, producing 24 g of a tacky solid. 20 g of water was added to 5 g of this tacky solid, the resulting solution was evaporated to dryness, and then the resulting solids were recrystallized from water to yield light tan needle crystals of the trifluoroacetic acid salt of 5-fluoro-6-hydroxy-5,6-dihydrocytosine (328°C sublimation temperature). An infrared spectrum of this product was identical to that obtained in step A above, having a strong, broad OH absorption at 3 microns.

EXAMPLE 11

5-Fluorouracil)

A. 0.68 g of solid product obtained in Example A2 was sublimed at 190°C and 1 mm Hg pressure, producing 0.26 g of 5-fluorouracil of high purity.

B. 1.53 g of solids obtained in Example A2 above was placed in a reflux flask and then 5 ml of concentrated HCl was added to the flask. The flask contents were heated to the refluxing temperature, with formation of a precipitate. Filtration at 0°C yielded 0.27 g of 5-fluorouracil.

EXAMPLE 12

0.25 g of 5-fluoro-6-methoxy-5,6-dihydrouracil obtained in Example 1B above was placed in a reflux flask and then 1 ml of concentrated HCl was added to the flask. The flask contents were brought to refluxing temperature, and the precipitation of a solid soon occurred, producing 0.1 g of 5-fluorouracil.

EXAMPLE 13

0.43 g of 5-fluoro-6-(2,2,2-trifluoroethoxy)-5,6-dihydrouracil obtained in Example 2B was placed in a reflux flask and then 1 ml of concentrated HCl was added to the flask. When the flask contents were brought to refluxing conditions, precipitation of a solid occurred. The flask was cooled to 0°C, and the contents were filtered and washed with acetone, producing 0.12 g of 5-fluorouracil.

EXAMPLE 14

Example 13 were repeated, substituting 5-fluoro-6-acetoxy-5,6-dihydrouracil obtained in Example 3 for the 5-fluoro-6-(2,2,2-trifluoroethoxy)-5,6-dihydrouracil. The product obtained was 5-fluorouracil.

EXAMPLE 15

0.41 g of 5-fluoro-6-isopropoxy-5,6-dihydrouracil was placed in a reflux flask and then 1 ml of concentrated HCl was added to the flask. Precipitation of a solid occurred a few minutes after reaching reflux conditions, yielding 0.21 g of 5-fluorouracil.

EXAMPLE 16

Example 15 was repeated, using 5-fluoro-6-hydroxy-5,6-dihydrouracil obtained in Example 5 for the 5-fluoro-6-isopropoxy-5,6-dihydrouracil. 5-fluorouracil was obtained as the product.

EXAMPLE 17

0.45 g of 5-fluoro-6-(1,1,1,3,3,3-hexafluoroisopropoxy)-5,6-dihydrouracil produced in Example 7 was placed in a reflux flask to which was added 1 ml of concentrated HCl. The solid uracil compound did not dissolve completely in the acid. The flask contents were refluxed for about 5 minutes, cooled to 0°C, filtered, and washed with acetone to produce 5-fluorouracil.

Based on the preceeding examples, it appears that other uracil and cytosine derivatives may be prepared by substituting the appropriate material for the starting pyrimidine compound. For instance, aryl group-substituted pyrimidine derivatives have not been discussed in the foregoing description, as these materials are not now commercially available, but it is believed possible to obtain 5-fluorouracil derivative starting materials of Formula II but having aryl substituents or substituted aryl substituents in the 1,3,5 and/or 6 positions, and 5-fluorocytosine derivative starting materials having aryl substituents or substituted aryl substituents in the 1,5 and/or 6 positions, which should undergo the reaction described hereinabove to produce the corresponding 5-fluoro, 6-fluoro or -acyloxy, aryl substituted uracil and cytosine compounds. Representative aryl groups include phenyl and ortho-metha-and para-substituted phenyl groups having one or more substituents as —NO₂, —SO₃H, —SO₃Na, —NH₂, —OH, halogen, and the like. In a like manner, starting pyrimidine materials having the 1 and/or 3 nitrogen atoms substituted with lower alkyl groups, including halogenated alkyl groups, have not been described hereinabove, but these compounds should likewise undergo the above described reaction and are therefore believed suitable as starting materials in the process of the present invention.

In addition to the above-described ring nitrogen substituted pyrimidine compounds, it appears likely, from the results obtained hereinabove, that cytosine derivatives having substituents, such as lower alkyl radicals and the like, including halogenated alkyl radicals, on the nitrogen atom attached to the 4-carbon atom should also be appropriate starting materials for the process of the present invention, producing the corresponding 4-substituted amino-5-fluoro-6-substituted pyrimidine compounds.

2-thiouracil and 2-carboxymethylthiouracil are known compounds and are suggested, together with other pyrimidine derivatives wherein the oxygen atom on the 2-position carbon atom has been replaced by a sulphur atom or a substituted thio group, as suitable for undergoing a fluorination reaction, in the aforesaid copending application filed on even date herewith, to produce the corresponding 2-thio or 2-substituted thio compounds of Formula II, which compounds should in turn, undergo the reaction described hereinabove to produce compounds of Formula I, wherein the 2-position carbon atom carries a sulphur atom or a substituted thio group. In addition to the above, the arabinosides of compounds of Formula II, as well as other N-glycosides of the compounds of Formula II, should undergo the above described reaction, and are therefore believed suitable starting materials for the process of the present invention, to produce the corresponding N-glycosides of compounds of Formula I.

In addition, the results obtained hereinabove (note especially Example 9) suggest that certain classes of alkali metal compounds can also be used as the nucleophilic reagent. Such alkali metal compounds include acid salts, alcoholates, and alkali metal or alkaline earth metal cyanides or nitrites. Suitable alkali metal or alkaline earth metal compounds include those of the formula D'Q, wherein Q represents an alkali metal or alkaline earth metal, such as sodium, potassium, lithium, calcium, magnesium, barium and the like, and D' represents
—OR'

—CN
—NO₂
wherein R' has been defined above. The preferred compound of the above formula is sodium cyanide.

The alkali metal or alkaline earth metal nucleophilic reagent can be reacted with 6-substituted-5-fluoropyrimidine compounds of Formula II using the same reaction conditions as described hereinabove for the nucleophilic reagents of the formula T"H.

From the above, it will be appreciated that the results obtained to date suggests that compounds broadly of the general formula

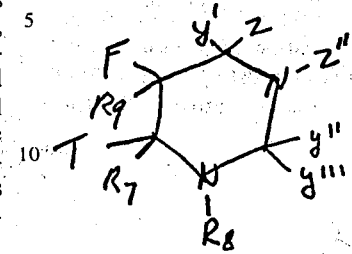

FORMULA IV wherein $R_9$ is hydrogen, fluorine, chlorine, bromine, lower alkyl, aryl, alkaryl or aralkyl, $R_7$ is hydrogen, lower alkyl, aryl, alkaryl or aralkyl, $R_8$ is hydrogen, lower alkyl, aryl, alkaryl, aralkyl or a glycoside radical, Y' is

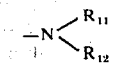

and Z and Z" together are a 3,4-double bond, or else Y' and Z, taken with the 4-carbon atom, is carbonyl and Z" is hydrogen, lower alkyl, aryl, alkaryl or aralkyl, wherein $R_{11}$ and $R_{12}$ are independently hydrogen, alkyl, aryl, alkaryl or aralkyl, Y" and Y''' taken together are = O or = S, or else Y" is hydrogen and Y''' is —S—(CH₂)ₙ''—COOH, wherein n" is a value from 1–4 and T has been described hereinabove (The term "lower alkyl" refers to alkyl groups and halogen-substituted alkyl groups which can be straight or branched chains, having 1 – 6 carbon atoms. The aryl, alkaryl and aralkyl groups mentioned above contain from 6 – 14 carbon atoms, such as phenyl, benzyl, naphthyl, tolyl, phenethyl, xylyl, and the like) can be reacted with the above-described reagents of the formula T"H or D'Q, under the reaction conditions described hereinabove, to produce compounds of the formula

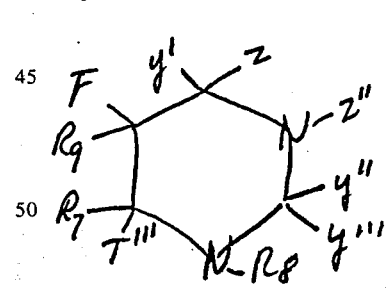

FORMULA V wherein $R_7$, $R_8$, $R_9$, Y', Y", Y''', Z and Z" have been described hereinabove, and T'''' is T" or D'.

Compounds of Formula V wherein at least one of $R_8$ and $R_9$ is hydrogen should also undergo the elimination reaction described above, by either sublimation, heating, or by heating in the presence of a strong acid, to remove the T''' and a hydrogen substituent and replace same with a 5,6-double bond or a 1,6 double bond (if $R_9$ is not hydrogen) on the compounds of Formula V. The elimination conditions described hereinabove should also be applicable for this broader class of 5-fluorinated pyrimidine compounds.

A number of pyrimidine derivatives, including 5-fluoro-uracil derivatives, have herbicidal properties, and the compounds of the above broad formula should likewise exhibit herbicidal effects. In addition, these compounds should also be useful as germicidal and antineoplastic agents.

What is claimed is:

1. A process for the preparation of 5-fluoro-6-substituted pyrimidine derivatives consisting essentially of reacting at least one pyrimidine derivative of the formula

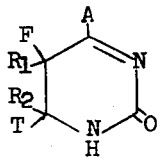

wherein A is —OH or —$NH_2$, $R_1$ is hydrogen, fluorine, chlorine, bromine or lower alkyl and $R_2$ is hydrogen or lower alkyl, and T is fluorine or lower acyloxy, wherein one or more hydrogen atoms may be substituted by halogen atoms, at a temperature of about —10 to about 72°C., with a compound having the formula T''H wherein T'' is —OH, —OC($R'$)$_3$, —SR, —OOCR', —NRR' or mixtures thereof wherein R is selected from the group consisting of lower alkyl and lower cycloalkyl, wherein one or more hydrogen atoms of the alkyl, or cycloalkyl may be replaced by fluorine, chlorine, or bromine atoms, and each R' is independently R or hydrogen, and wherein T'' differs from T, to produce a pyrimidine compound of the formula:

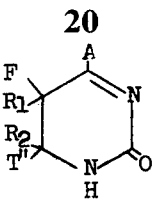

wherein A, T'', $R_1$ and $R_2$ are defined hereinabove.

2. Process according to claim 1, wherein T is lower haloacyloxy.

3. Process according to claim 2, wherein T is lower fluoroacyloxy.

4. Process according to claim 1 wherein T is fluorine.

5. Process according to claim 1, wherein said temperature is 20° to 60°C.

6. Process according to claim 5 wherein said temperature is about room temperature.

7. Process according to claim 1 wherein the molar ratio of said compound of formula T''H to said pyrimidine derivative is no greater than 100:1.

8. Process according to claim 7, wherein said molar ratio is 1.01:1 to 10:1.

9. Process according to claim 1, wherein said pyrimidine derivative, prior to said reaction, is in dry solid form.

10. Process according to claim 1, wherein T'' is —OC($R'$)$_3$.

11. Process according to claim 10, wherein A is —OH and $R_1$ and $R_2$ are both hydrogen.

12. Process according to claim 1, wherein said pyrimidine derivative is a mixture of 5-fluoro-6-trifluoroacetoxy-5,6-dihydrouracil and 5,6-difluoro-5,6-dihydrouracil.

* * * * *